(12) United States Patent
Koster et al.

(10) Patent No.: US 6,465,778 B1
(45) Date of Patent: Oct. 15, 2002

(54) IONIZATION OF HIGH-MOLECULAR SUBSTANCES BY LASER DESORPTION FROM LIQUID MATRICES

(75) Inventors: Claus Koster, Lilienthal; Jochen Franzen, Bremen, both of (DE)

(73) Assignee: Bruker Daltonik GmbH, Bremen (DE)

(*) Notice: Subject to any disclaimer, the term of this patent is extended or adjusted under 35 U.S.C. 154(b) by 0 days.

(21) Appl. No.: 09/364,244

(22) Filed: Jul. 29, 1999

(30) Foreign Application Priority Data

Jul. 29, 1998 (DE) .......................................... 198 34 070

(51) Int. Cl.[7] .................................................. H01J 44/04
(52) U.S. Cl. ......................................................... 250/288
(58) Field of Search .................................. 250/287, 288

(56) References Cited

U.S. PATENT DOCUMENTS

| | | | |
|---|---|---|---|
| 5,118,937 A | | 6/1992 | Hillenkamp et al. |
| 5,506,348 A | | 4/1996 | Pieles |
| 5,589,685 A | * | 12/1996 | Wu et al. ................. 250/282 |
| 5,595,636 A | * | 1/1997 | Franzen ..................... 204/464 |
| 5,705,813 A | * | 1/1998 | Apffel et al. ............. 250/288 |
| 5,770,860 A | * | 6/1998 | Franzen ..................... 250/288 |
| 5,841,136 A | * | 11/1998 | Holle et al. .............. 250/288 |
| 6,104,028 A | * | 8/2000 | Hunter et al. ............. 250/288 |
| 6,175,112 B1 | * | 1/2001 | Karger et al. ............. 250/288 |
| 6,287,872 B1 | * | 9/2001 | Schurenberg et al. ....... 436/181 |
| 6,331,702 B1 | * | 12/2001 | Krutchinsky et al. ....... 250/281 |

FOREIGN PATENT DOCUMENTS

GB 2312782 A 11/1997

OTHER PUBLICATIONS

Cornett, Shannon D. et al.; Liquid Mixtures for Matrix–Assisted Laser Desorption; Anal. Chem. 1993, 65, pp. 2608–2613.

Tanaka, Koichi et al.; Protein and Polymer Analyses up to m/z 100 000 Spectrometry; Rapid Communications in Mass Spectrometry, vol. 2, No. 8, 1988, pp. 151–153.

Berkenkamp, Stefan et al.; Infrared Maldi Mass Spectrometry of Large Nucleic Acids; Jul. 10, 1998, vol. 281; Science, pp. 260–262.

* cited by examiner

*Primary Examiner*—Kiet T. Nguyen

(57) ABSTRACT

The invention relates to ionization with low fragmentation and adduct formation, of high-molecular analyte molecules, particularly of large biopolymers, by matrix-assisted laser desorption (MALDI) from liquid matrices for mass-spectrometric analysis of the resulting ions, particularly for determination of their molecular weight. The invention uses liquids as matrix substances with very low vapor pressures from the group of minimally trihydroxylic alcohols with at least one ether bond (ether polyols or polyether polyols). These can be used advantageously for energy absorption and ionization by infrared lasers (IR-MALDI), however other lasers, such as conventional. UV lasers, can be used for other wavebands by the addition of light-absorbing compounds.

22 Claims, 2 Drawing Sheets

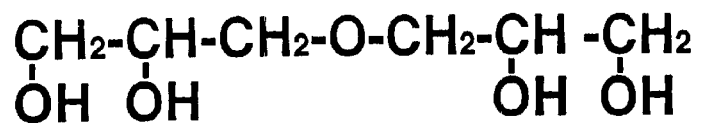
Figure 1
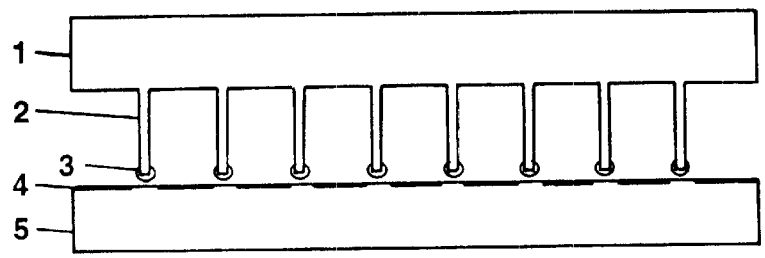
Figure 2
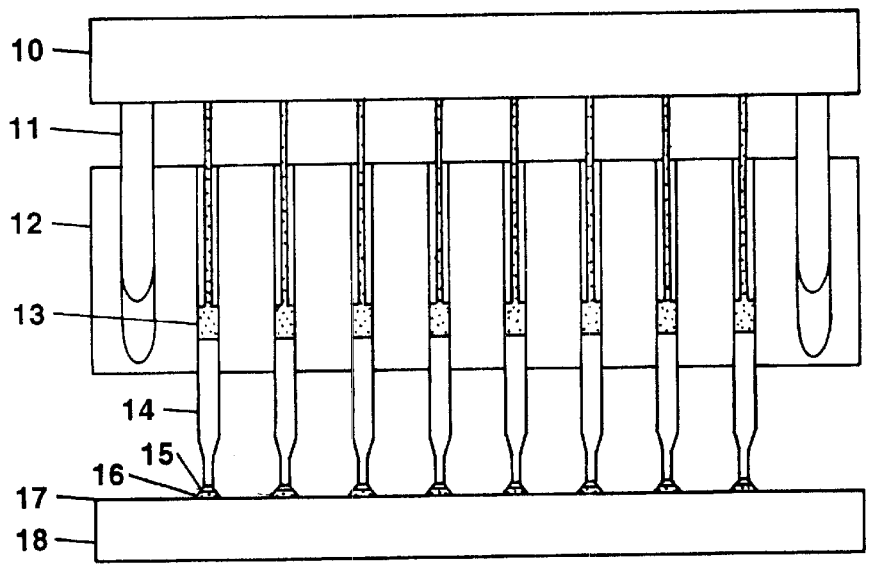
Figure 3
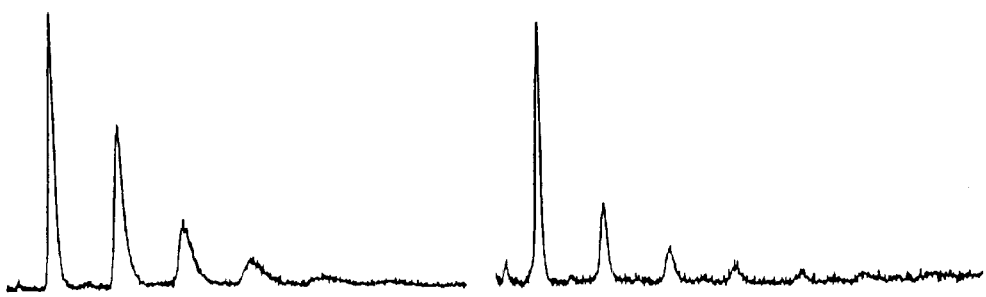
Figure 4a
(LYSOZYME IN GLYCEROL)
Figure 4b
(LYSOZYME IN DIGLYCEROL)

IONIZATION OF HIGH-MOLECULAR SUBSTANCES BY LASER DESORPTION FROM LIQUID MATRICES

The invention relates to ionization with low fragmentation and adduct formation, of high-molecular weight analyte molecules, particularly of large biopolymers, by matrix-assisted laser desorption (MALDI) from liquid matrices for mass-spectrometric analysis of the resulting ions, particularly for determination of their molecular weight.

PRIOR ART

For mass-spectrometric determination of the molecular weight of biomolecules or other high polymers, ionization by means of matrix-assisted desorption with the aid of a pulsed UV laser (MALDI) has been established as a standard method in spite of some disadvantages. MALDI is also used for structural determination, generally then with desirable fragmentation of the molecule ions by taking special measures.

Normally, lasers are used which operate within the ultraviolet light range and emit light pulses lasting a few nanoseconds, such as simple and inexpensive nitrogen lasers with 337 nanometer wavelength and two to three nanoseconds light pulse length. The pulsed generation of ions calls for the use of time-of-flight mass spectrometers (TOF-MS) for analysis, although ion storage mass spectrometers such as ion cyclotron resonance mass spectrometers (FT-ICR=Fourier-transformation ion cyclotron resonance) or high frequency quadrupole ion trap mass spectrometers can also be used successfully.

Biomolecules in this context are the oligonucleotides (i.e. the genetic material in its various forms such as DNA or RNA), proteins and polysaccharides (i.e. the essential building blocks of the living world), including their particular analogs and conjugates, such as glycoproteins or lipoproteins. Other high polymers in particular are the artificially produced polymers. In the following, these biopolymers and artificial polymers, the molecules of which are to be analyzed, are simply called the "analyte."

The selection of matrix substance for MALDI depends on the type of analyte molecules; in the meantime, several hundred various matrix substances have become known which are each suitable for specific groups of analyte molecules. The matrix substance in particular has the following tasks: 1) to bond the sample substance in a finely distributed, very dilute form to the sample support, 2) to absorptively collect the energy from the laser beam, 3) to blow the analyte molecules individually into the gas phase by creating a vapor cloud, and 4) to ionize a portion of the analyte molecules by means of protonation or deprotonation. During this process of vaporization and ionization, neither should the analyte molecules decompose, nor should matrix or other molecules attach themselves to the analyte ions to a larger extent, since determination of the correct molecular weight is no longer possible in either case.

It has generally proven favorable to use aromatic acids as matrix substances that are crystalline in a normal state, and to integrate relatively few analyte molecules into the small matrix crystals or at least imbed them in the boundary surfaces between the small crystals. The bio-molecules are generally at least weakly water soluble so it is preferable, though not necessary, to use water soluble matrix substances. A rule of thumb has been developed which states that the selection of matrix substances becomes more difficult, the higher the molecular weight of the biosubstances is. Either fragmentation of the macromolecules increases to such an extreme degree that molecule ions can no longer be found, or adducts with matrix or other molecules are formed so that it is hardly possible to determine the molecular weight. In many cases, a mixture of adduct formation and splitting off of smaller fragments causes the mass-spectrometric signal to become a broad peak, which makes precise mass determination no longer possible.

In constantly searching for new matrix substances more favorable for certain substance categories, it has almost been forgotten that the first MALDI ionization of high-molecular substances was observed in a liquid glycerol matrix, to which a fine metallic powder was added for the absorption of UV laser beams (K. Tanaka et al., Rapid Comm. in Mass Spectrom., 2, 151, 1988). As MALDI was further developed, glycerol was used only occasionally as the matrix due to the disadvantages described below, but also in particular because glycerol cannot be excited directly by the standard UV lasers. In principle, however, this disadvantage was eliminated by a working group dissolving UV absorbents within the glycerol and thus adapting the liquid mixed matrix to the standard UV lasers, although, for unknown reasons, not all the absorbents displayed good results, and some strong UV absorbents actually prevented ionization (D. S. Cornett et al., "Liquid Mixtures for Matrix-Assisted Laser Desorption", Anal. Chem., 65, 2608, 1993).

In a very recent article, an infrared laser was used for ionization, the radiation of which was capable of directly exciting one of the stretching vibrations of the glycerol ("Infrared MALDI Mass Spectrometry of Large Nucleic Acids", Science 281, 2212, 1998). In particular, the radiation from an erbium-YAG laser with 2.94 micrometers wavelength excites the stretching vibrations of the OH groups. It was established that this combination of glycerol and infrared radiation with extremely low-energy photons is capable of extraordinarily sensitive, low-fragment ionization of molecules with extremely high molecular weights. Although the erbium-YAG infrared laser, most favorable for absorption of radiation, is indeed still relatively expensive and technically not yet particularly reliable, it can be expected that this type of laser will go through development similar to efficient equipment like the related neodym-YAG laser.

Glycerol is at all suitable for this type of ionization because it has a relatively low vapor pressure. Even in a vacuum, a small droplet of about one microliter evaporates quite slowly, taking about one half hour to dry out completely. This time can be utilized for MALDI analysis of several samples on a carrier plate.

Glycerol was used already one or two decades ago as a liquid medium for the ionization of dissolved substances by means of bombardment with fast neutral particles (fast atom bombardment, "FAB"). Using this method, highly sensitive, very low fragment and low adduct spectra of molecules with relatively high molecular weights were obtained.

So far there can only be speculation about the reason for the similarly high ionization effect of glycerol in these very diverse ionization methods. It appears possible that macromolecules which are almost always composed of mixed hydrophobic and hydrophilic groups (amphiphitic substances) prefer to keep their more hydrophobic side toward the surface, and project their hydrophilic side toward the very polar solution. This effect may lead to a substantial increase in the concentration of these high polymers at the surface. On the other hand, glycerol (1,2,3-propantriol) as a trihydroxylic alcohol may possibly ionize other substances very easily by means of proton donation from one of the alcohol groups. Even shockwaves propagated in the liquid with a shaking off of surface molecules has been discussed. It is also known that very polar water may be used as a matrix, but it requires extreme cooling of the carrier plates within a vacuum to prevent immediate evaporation.

Ionization by means of glycerol offers advantages, but also severe disadvantages.

Advantages: In addition to the high sensitivity for very large molecules and the relatively low fragmentation and adduct-formation, the uniform ionization yield over the entire drop surface is especially prominent on the list of advantages. Since visual control of the bombardment site is no longer necessary, and automated procedure is possible, different than the case previously for MALDI procedures where droplets are dried into solid matrices. Also considered advantageous is the fact that samples are relatively easy to prepare; a droplet with aqueous analyte solution may simply be applied to a droplet of glycerol. The preparation is conducted very simply in pipetting machines. The water evaporates (to a large extent at least) when introduced into the vacuum of the mass spectrometer.

Disadvantages: Prominent on the list of disadvantages are the relatively short time available for use and the extreme load on the vacuum system; due to both this vacuum load as well as its short time available for use, hundreds of samples unfortunately cannot be analyzed on a sample support using this method. A detectable load on the vacuum system, and thus also on the quality of the spectra, occurs with only ten samples on a support, and the quality is affected by the poor pressure within the spectrometer. This runs counter to the increasing demand for a high sample throughput where not just ten, but rather a thousand samples are required on a sample support. This disadvantage can be offset by extreme cooling of the sample support plate outside of the vacuum, in the sample support lock, and within the vacuum, although such cooling is difficult (the carrier plate is at a potential of 30 kV in the mass spectrometer) and not available in commercial mass spectrometers.

Of course, for this high analysis sample throughput, it is essential not only for the MALDI ionization to be automatable, but also for all the analysis steps including preparation of the samples. However, as already mentioned above, this is exactly the case when glycerol is used as the matrix substance, and it is generally better than when solid matrix substances are used.

IDEA OF THE INVENTION

The invention consists of using liquid matrices made up of multihydroxylic (at least trihydroxylic) alcohols for MALDI, which however possess a substantially lower vapor pressure compared to the glycerol presently used by extension of the carbon chains and integration of at least one ether bond. Diglycerin, Triglycerin, and Polyglycerin (trivial names, supplier: Solvay Alkali GmbH, Dilsseldorf; in the following designated as diglycerol, triglycerol, and polyglycerol) belong to this group of liquids. Here, the matrix molecules may be directly excited by use of infrared lasers, or adapted to other types of lasers by resolving absorbents for light at other wavelengths.

It has been shown in experiments that a large portion of OH groups (hydroxy groups) is vital for the functioning of a MALDI matrix substance. On the one hand (in addition to the chain extension itself), the large share of these alcoholic OH groups contributes to reduction of the vapor pressure, but it also appears to be important for energy consumption, for concentration of analyte molecules at the surface and for ionization. In the case of erbium-YAG lasers, these hydroxy groups are also particularly helpful in the direct consumption of energy from the laser radiation.

Tetrahydroxylic alcohols of normal hydrocarbons (the simplest sugars) are already solid, thus the basic idea of the invention of using liquids rich in hydroxy groups with extremely low vapor pressure cannot be realized with normal hydrocarbon alcohols. The integration of ethereal bonds in the carbon chains do however keep higher alcohols liquid, so that matrix liquids of the type according to the invention can be verified by means of ether polyols, or by polyether polyols.

Belonging particularly to these compounds are tetravalent diglycerol (trivial name) with the structure $HOH_2C$—$HOHC$—$H_2C$—$O$—$CH_2$—$CHOH$—$CH_2OH$ or the pentavalent triglycerol $HOH_2C$—$HOHC$—$H_2C$—$O$—$CH_2$—$CHOH$—$H_2C$—$O$—$CH_2$—$CHOH$—$CH_2OH$, which has two ether bonds. The structure resembles so-called polyethylene glycols, which are used as ultra high vacuum pump oils due to their extremely low vapor pressure, although in spite of relatively long chain lengths, they represent only dihydroxylic, terminal alcohols and have proven in experiments to be unsuitable for the present purpose.

Diglycerol, triglycerol and higher polyglycerols, including those of an asymmetrical type (such as glycol glycerol joined by an ether bond), are all referred to here under the term polyglycerols for purposes of simplification.

The polyglycerols are miscible with water and can dissolve practically all analyte molecules if only introduced in sufficiently low concentrations. The solubility for many substances, such as for some favorable UV absorbents, is greatly reduced however with a higher degree of polymerisation. Due to its miscibility with water, a method can be used in which the polyglycerols are first applied to the carrier plates, onto which the aqueous analyte solutions are then simply pipetted. The polyglycerols have a thick, oily consistency, similar to honey at a higher degree of polymerisation. However, different than oils, they very easily wet hydrophilic surfaces due to their strong polarity; they can therefore be applied to MALDI carrier plates simply by using multi-needle heads.

The vapor pressure is already so low for diglycerol that either 96 or 384 samples can be applied, for example, without substantially disturbing the mass spectrometer vacuum. Even the application of 1,536 small-area samples is possible. These numbers correspond to the numbers of reaction containers in the standard micro-titration plates for parallel preparation of samples in biochemistry.

It has also proven advantageous if the carrier plates are already provided with a hydrophobic basic pattern that has hydrophilic anchorage areas for the polyglycerols. The anchorage areas should be large enough that the polyglycerols form very flat droplets. Droplets of about one millimeter diameter and about 0.2 to 0.4 millimeters height are advantageous, for example. Such a basic pattern on the carrier plate with hydrophobic marginal areas for the droplets prevents the pipetted water droplets with analyte molecules from polyglycerols from flowing over to adjacent areas of the carrier plate before they can be detached. The sample spots, and thus also the evaporation rate of the polyglycerols, stay very small. On a 78 by 114 millimeter carrier plate (size of micro-titration plates), 1,536 sample spots can thus be easily applied.

Already for diglycerol, and even more so for triglycerol, the pressure within the mass spectrometer is barely influenced even if large numbers of small-area samples are applied to a sample support. For diglycerol, the droplets' shrinkage is only barely perceptible even when kept for an entire day within the vacuum. Thus analysis times of at least a day can be realized. This allows analysis times of about one minute for each sample with 1,536 samples, much more than necessary.

The water from the aqueous solution of analyte molecules is conveniently evaporated out of the sample spots for practical reasons before introducing the carrier plates into the vacuum of the mass spectrometer's ion source. This evaporation of water should be conducted carefully since remnants of water occasionally can lead to explosion of the droplets during laser bombardment. The evaporation may occur under reduced pressure and should be supported by careful heating of the carrier plate to temperatures of 80 to 130° C. (depending on the type of analyte molecules). In this way, evaporation can proceed in the vacuum lock of the mass spectrometer although a special vacuum chamber is more favorable for this purpose due to the extended period of the evaporation process.

Liquid matrices according to the invention, with extremely low vapor pressure, can also be exploited advantageously in entirely different applications. Thus it is possible to apply these matrix liquids to blot membranes, which are charged in a known manner by blotting with electrophoretically, two-dimensionally separated proteins from PAGE plates (PAGE=polyacryl gel electrophoresis). The protein molecules adsorbed on the porous surface structures of the blot membranes are partially detached by the matrix liquids and applied to their surface by difflusion. Here, by controlling the viscosity via temperature and water content, it is possible to disturb the special separation of the proteins as little as possible. A capacity for storage can be achieved by evaporation of the water and freezing of the matrix liquid. Highly sensitive analysis proceeds by means of MALDI ionization directly from the blot, membrane stretched onto a carrier plate, or by simple transfer (imprinting, stamping) of the matrix liquid onto a special carrier plate and, by means of two-dimensional array analysis, by corresponding movement of the carrier plate.

DESCRIPTION OF THE FIGURES

FIG. 1 shows the structure of diglycerol, a preferred matrix liquid.

FIG. 2 shows the application of matrix liquid droplets (3), using a simple die head (1) which 10 has many metal die needles (2) of exactly the same length, onto hydrophilic areas with hydrophobic marginal areas on the surface (4) of the carrier plate (5).

FIG. 3 illustrates the parallel application of individual samples (15) onto the matrix spots (16) on the carrier plate (18) by a multiple pipette (10). The multiple pipette has a parallel guide (11) within a pipette body (12), and a large number of individual pipettes (14) with 15 pistons (13). The surface (17) of the carrier plate (18) has hydrophilic anchorages and hydrophobic limitation areas for the matrix spots which prevent spreading of matrix liquid and sample solution.

FIGS. 4a and 4b show the spectra of lysozyme (molecular weight 14,306.2 atomic mass units), generated using glycerol (left, 4a) and with diglycerol (right, 4b). By using relatively high concentrations of analyte molecules, dimers, trimers, tetramers, pentamers and hexamers are formed which demonstrate the extremely gentle ionization in both matrix liquids. As already shown by Cornett et al., it is possible to produce extremely sharp monomer peaks by reducing the concentration without oligomers being visible.

PARTICULARLY FAVORABLE EMBODIMENTS

Figure 5:
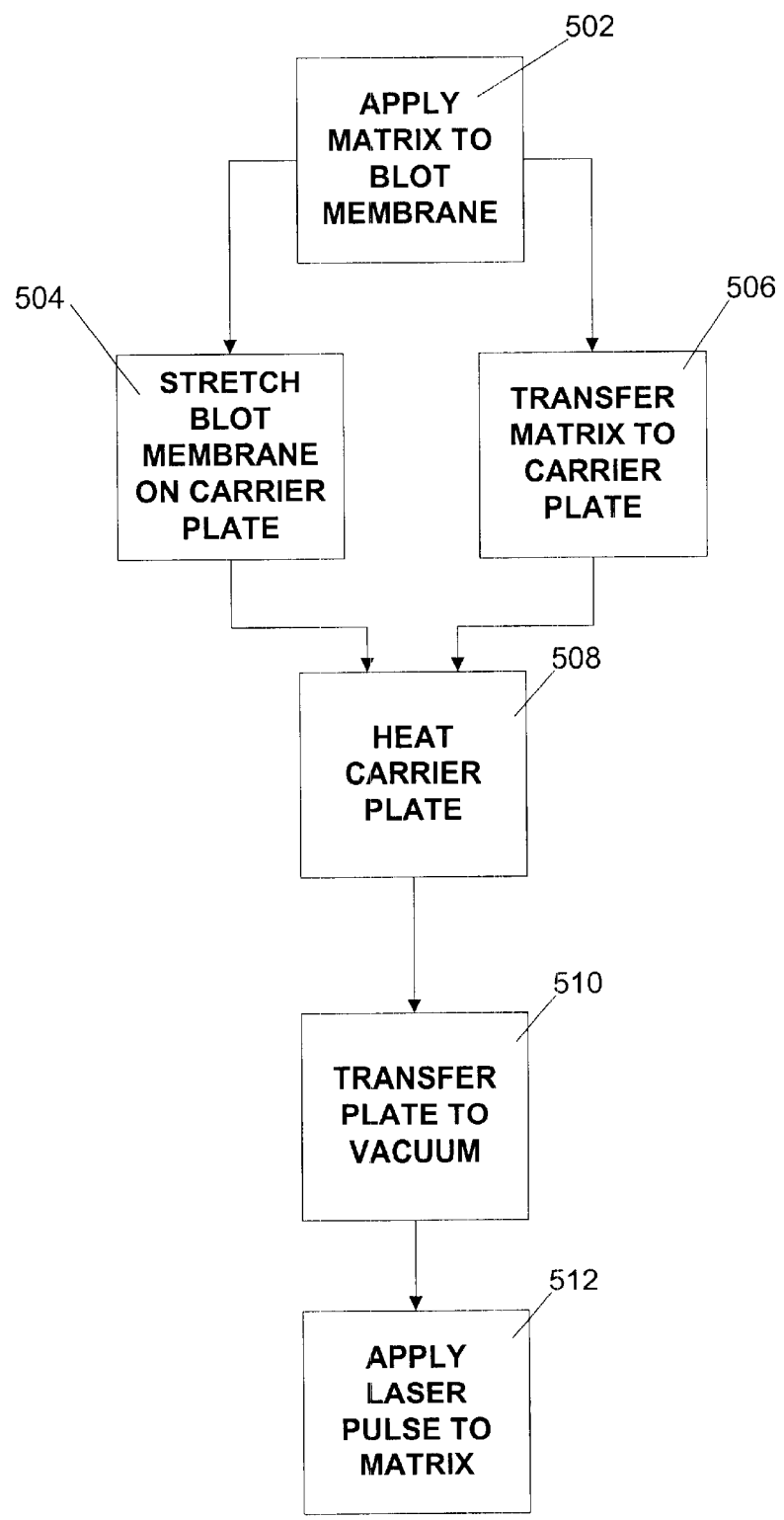
FIG. 5 is a flow diagram that depicts one possible set of steps that may be followed in using the present invention.

An especially favorable embodiment of the method is already indicated by the application of diglycerol (structure in FIG. 1) instead of the formerly used glycerol as a matrix liquid. The analytical properties within the MALDI process are very similar, as can be seen in FIGS. 4a and 4b. Diglycerol is a tetrahydroxylic alcohol with ether bond, has a slightly oily consistency, is miscible with water, and produces similarly good mass spectra as glycerol being bombarded by an erbium-YAG laser. The energy density at the laser focus must be set slightly higher than for glycerol, to take account of the higher boiling point of diglycerol. The influence of the vacuum by the diglycerol is much better however: In this way, many more sample droplets can be applied and longer analysis times supported. Diglycerol droplets barely decrease in size even after a day within a vacuum.

By dissolving UV absorbents in the liquid matrix substances, it is possible to continue using the standard UV lasers, for example the standard nitrogen lasers with 337 nanometers wavelength and 3 nanoseconds pulse width. Practically all MALDI mass spectrometers commercially available up to now are equipped with these lasers. Matrix substances formerly used for UV lasers, such as α-cyano-4-dehydrocinnamic acid, can be used as UV absorbents for example. Since the absorbents no longer need to take over the ionization, completely different types of UV absorbents can also be used. It is even possible to adapt to a laser with visible light.

Use of triglycerol is also possible, although the consistency here is already much thicker and the solubility for UV absorbents is also considerably lower. However, the vapor pressure of the polyglycerols can be further reduced by means of other chemical groups, for example by partial nitration, without forming solid substances under normal conditions. By means of deflagration support, partial nitration may also have a favorable effect on the MALDI process. Other chemical groups may also have a favorable effect on the MALDI process. For example, chemical groups may be integrated which directly permit absorption of the laser light used.

| Properties: | Glycerol | Diglycerol | Triglycerol |
|---|---|---|---|
| Boiling point | 130° C. at 1.8 mbar | 205° C. at 1.3 mbar | >240° C. at 0.2 mbar |
| Viscosity at 20° C. | 1,412 mPas | 20,900 mPas | 86,400 mPas |

Viscosity drops drastically at higher temperatures. For instance for di- and triglycerol, viscosity is reduced by about 2.5 powers of ten when heated to 100° C.

Di- or triglycerol (and similar compounds) can be applied very easily and reliably to MALDI carrier plates using multi-head needle dies due to their oily viscosity and their wetting capacity for hydrophilic surfaces (see FIG. 2). Thus, 1,536 flat droplets of about 1 millimeter diameter can be easily applied to a metal plate with the dimensions 78 by 128 millimeters (size of micro-titre plates frequently used in biochemistry). The centers of the droplets are then at a distance of 2.25 millimeters from one another, corresponding to one of the sub-grid dimensions of micro-titre plates (the spacing of the basic grid on the micro-titre plates is 9 millimeters).

The 1,536 droplets can be applied using a 96-point needle head in 16 steps, using a 384-point needle head in 4 steps, or also using a 1,536-point needle head in just one step. The needle heads, with needles about 0.8 millimeters in diameter, are relatively simple to manufacture and produce spot sizes of about 1 millimeter diameter. Metal needles made of stainless steel, for example, are moderately hydrophilic and therefore pick up a flat drop each time when lifted from a supply container with polyglycerol, which does not drop off and can be transferred very well. The head can be used to imprint a larger number of carrier plates since the droplets do not hardly evaporate at all in air and thus allow the plates to be stored for a longer period of time.

The aqueous analyte solutions can then be taken out of micro-titre plates using commercially available pipetting machines and pipetted onto the polyglycerol droplets. There they mix diffusively with the polyglycerol.

To make the analyte solutions not sliding off of the polyglycerol droplets and flow onto the carrier plate before mixing takes place, it is practical to make the area of the carrier plate surrounding the polyglycerol droplet very hydrophobic. The polyglycerol droplets may be placed on top of hydrophilic anchorage spots here. They take precisely the shape and known position of the hydrophilic anchorage spot, favorable for an automatic MALDI method, which in this way does not need to search for the spots first. This hydrophobic structuring of the carrier plate is also important for keeping the sample spots small and therefore evaporation is extremely low.

Due to their strong polarity caused by the many OH groups, the polyglycerols react in exactly the same way to hydrophilic and hydrophobic surfaces as with strongly polar water. The surfaces of previously used metallic sample supports are usually slightly hydrophilic by nature, so that a sample droplet normally flows apart until a flat setting angle, determined by hydrophilia, is reached. The hydrophilia is produced by the hydroxy groups which form under. the influence of moist air on any metal (even on precious metals).

To maintain hydrophobic surfaces on the sample support, the entire sample support can be made of a hydrophobic material such as the fluoropolymer known by the name TEFLON, a registered trademark of E.I. Du Pont De Nemours and Company Corporation. However, it must then be ensured that the surface is electrically conductive (for example by imbedding with graphite), since the MALDI process requires a homogeneous electrical field, on the one hand for uniform acceleration of the ions formed, and on the other hand a lead for charges, the polarity of which is contrary to that of the ions formed. A pure graphite surface is also very hydrophobic.

It is certainly practical for purposes of simple manufacture to stay with metal or metallized plastic sample supports, while making the surface hydrophobic however. This can be done, for example, using a wafer-thin, hydrophobic lacquer, or by gluing on a thin, hydrophobic film made of TEFLON. However, it is even more practical to make the metal surface hydrophobic by means of a molecular, chemical change, since a certain electrical conductiveness is then retained, even if it is high-resistant.

Such hydrophobization of a metal surface is known. To do this, longer alkane chains (for example linear $C_{18}$ chains) are normally bonded covalently via a sulphur bridge to the atoms on the metal surface. This bond is extremely firm, and it cannot be washed away using normal agents. It can stand up to years of weathering. Even more hydrophobic surfaces can be produced if the hydrogen atoms are replaced by fluorine atoms at the ends of the alkane chains. However, there are many other equivalent methods of hydrophobization, for example using silicones, ceramic nanopowders, alkyl chlorosilanes or tin-organic compounds. Hydrophobic layers can also be generated by means of plasma coating.

The hydrophilic anchorage areas for the sample droplets can be generated in many ways. One example is covering the required anchorage area before hydrophobization with a lacquer that can be washed off or is hydrophilic. For example, coating lacquer may be shot on in the form of small droplets using a piezo-operated droplet pipette similar to an ink-jet printer. This allows extremely good locational precision for the lacquer points. After hydrophobization, the lacquer points may be simply washed away, unless they already create sufficiently good hydrophilic anchor points. The washed anchorage areas can also be made especially hydrophilic using special hydrophilization agents.

Such hydrophilic lacquer droplets can also be imprinted subsequently onto the hydrophobic surface. Amphiphilic substances are particularly suitable for this as they bond to the hydrophobic surface and create a hydrophilic surface.

The hydrophilic anchorage areas can also be produced in a very simple manner by destroying the hydrophobic layer. This can be done by imprinting (for example in the same manner as the ink-jet printer) chemically changing or enzymatically destructive substance solutions, by glowing-hot tips for destruction or also by ablation of the surface material, for example through spark erosion or laser bombardment.

The sample droplets from the analyte solution are normally applied with pipettes to the already applied polyglycerol spots on the sample support. For simultaneous application of many sample droplets from micro-titre plates, multiple pipettes are used that are moved by pipette robots in pipette machines (see FIG. 3). It is therefore favorable to use sample supports of the same size as the micro-titre plates and, as already mentioned above, adapt the grid of the hydrophilic anchorage areas to the grid of the micro-titre plates. It is also favorable if the sample supports have the same shape as the micro-titre plates since they can then be loaded by commercial pipette robots. Since a substantially higher sample density can be achieved on the sample support than is possible in the micro-titre plates, the grid on a sample support can be much finer than that which corresponds to the grid of the micro-titre plates. This can, for example, be achieved by division of the grid on a micro-titre plate. Then samples from several micro-titration plates can be applied to one sample support. The basic grid of the original micro-titre plate consists of 96 small containers in a grid of 9 millimeters arranged in 8 rows by 12 columns. Micro-titre plates have continued to be developed, but without changing their size, and modem designs now have 384 or even 1,536 microcontainers in a grid of 4.5 and 2.25 millimeters.

Application of the analyte droplets onto the polyglycerol droplets is performed conveniently if the tips of the multiple pipettes are placed at a distance of 200 to 500 micrometers above the sample support. About 100 to 500 nanoliters of sample solution are pipetted from every pipette tip of the multiple pipette onto the sample support. Even if there is a horizontal mismatch of the pipette tips, the droplets can still reach their respectively assigned polyglycerol spot via the hydrophilic anchorage area and attach themselves there. When lifting away the multiple pipette, the droplets remain on the sample support since they have found their anchorage point there.

Of course the droplets may also be applied manually, just as there are many other application possibilities for the method described here, as will be apparent to any specialist in this field according to this design.

It is also of course possible to mix the analyte solution with the polyglycerol in the sample container, for example in the sample container on the micro-titration plates, with subsequent pipetting over to the sample support, although this procedure is regarded as less favorable here.

A completely different method of application for liquid matrix substances according to the invention concerns the analysis of proteins or oligonucleotides which have been separated electrophoretically in gels one- or two-dimensionally. The known two-dimensional separation of biopolymers according to their isoelectric point on the one hand, and according to their electrophoretic mobility in gel on the other hand, is frequently performed on polyacryl gels, as well as on other gels. The biopolymers from the gels are regularly transferred after their separation by means of so-called blotting (usually electrophoretic electroblotting) onto thin blot membranes made of nylon, nitrocellulose, PVDF or other porous-adsorptive materials where they can be stored for long periods of time after drying. Analysis by means of dyeing methods (Western, Southern, Northern Blotting) can only make the most intensive proteins, DNA or RNA visible however, and analytical methods with higher dynamic measurement ranges are still being sought.

The matrix liquids according to the invention thus permit a mass-spectrometric MALDI analysis of the lateral divisions of various types of biopolymers, for example directly from the thin blot membranes. To do this, the matrix liquid must first be applied to the blot membranes without allowing the proteins an opportunity for strong lateral diffusion. This can be done, for example, by electrospraying the matrix liquids at a very high temperature (such as greater than 100° C.), since very low viscosity is achieved at these temperatures and the liquids can be sprayed like water. Droplets at a high temperature dissolve a part of the adsorbed proteins from their adsorption base. Very rapid cooling to normal ambient temperatures then freezes the lateral distribution of the proteins while hardly disturbing the local resolution. Even changing the viscosity by the addition of water may be used for this purpose. The water can be removed again by evacuation.

The blot membranes prepared in such a way can be stretched directly onto the carrier plates and analyzed by means of suitable scanning methods under respectively pointed MALDI ionization within the mass spectrometer. However, the blot membranes can also be brought into direct contact with carrier plates, whereby a part of the sticky matrix liquid remains on the carrier plate after the blot membrane is carefully pulled away and can then be analyzed massspectrometrically as to the proteins they contain. This transfer can be made very effective by skillful exploitation of temperature differences without disturbing the lateral resolution of the protein distribution. It is even possible to force separation of the matrix liquid on the carrier plate into very fine droplets by means of a very fine, hydrophilic-hydrophobic grid on the carrier plate, thus completely preventing further lateral diffusion of the proteins.

It must be emphasized here that all these types of analyses are only made possible by the extremely low vapor pressure of the matrix liquids according to the invention. Application of simple glycerol, as it was previously used, does not permit this procedure since the vacuum in the mass spectrometer is too severely inhibited and there is no opportunity for a longer analysis time to scan many samples or larger surfaces due to the rapid drying.

FIG. 5 shows one possible set of steps involved in the inventive process. Those skilled in the art will recognize that this is just one possible combination of the disclosed steps, and that other variations obviously exist. First, a matrix material is applied to a blot membrane (step 502). The matrix is then transferred to the carrier plate. Two alternative methods of doing this are shown in the figure: stretching the blot membrane on the plate (step 504); or applying the matrix to the plate from the blot membrane (step 506). The plate may then be heated to promote evaporation (step 508) and the plate transferred to the vacuum (step 510). Finally, the laser pulse is applied to the matrix as part of the MALDI ionization procedure.

What is claimed is:

1. A method of ionizing an analyte substance, the method comprising:

applying an analyte substance and a liquid matrix to a sample location of a carrier plate, wherein the liquid matrix comprises a multihydroxylic alcohol with at least one ether bond in a carbon chain of the multihydroxylic alcohol;

transferring the carrier plate to a vacuum system; and applying a pulsed energy beam to the matrix.

2. A method as in claim 1, wherein the matrix comprises at least one polyglycerol.

3. A method as in claim 1, wherein the pulsed energy beam is applied with an infrared pulsed laser.

4. A method as in claim 3, wherein the laser is an erbium-YAG laser.

5. A method as in claim 1, wherein the pulsed energy beam is applied by a laser and the method further comprises dissolving an absorbent substance in the matrix that is absorbing for wavelengths output by the laser.

6. A method as in claim 5, wherein the laser is a standard ultraviolet laser.

7. A method as in claim 6, wherein the absorbent substance is absorbent at ultraviolet wavelengths.

8. A method as in claim 1, wherein the matrix is applied to at least 96 locations on the carrier plate.

9. A method as in claim 1, wherein the analyte substance is mixed together with the matrix prior to being applied to the carrier plate.

10. A method as in claim 9, wherein the matrix liquid is located on the carrier plate prior to application of the analyte substance.

11. A method as in claim 10, wherein a plurality of droplets of the matrix are applied to the carrier plate simultaneously using a multiple die.

12. A method as in claim 10, wherein a droplet of the analyte substance is pipetted onto a droplet of the matrix.

13. A method as in claim 12, wherein a plurality of analyte droplets are simultaneously applied to the matrix droplets using a multiple pipette.

14. A method as in claim 10, wherein the carrier plate has hydrophilic areas surrounded by hydrophobic regions and the matrix substance is applied to the hydrophilic areas.

15. A method as in claim 1, wherein the matrix liquid, is applied to a blot membrane containing a biopolymer prior to being applied to the carrier plate.

16. A method as in claim 15, wherein the blot membrane containing the matrix is stretched onto a sample support.

17. A method as in claim 15, wherein the matrix is applied to the carrier plate from the blot membrane by contact with the carrier plate.

18. A method as in claim 1, further comprising evaporating liquid from the matrix after its application to the carrier plate.

19. A method as in claim 18, wherein the evaporation is facilitated by heating of the carrier plate.

20. A liquid matrix substance for use in ionizing an analyte substance during matrix assisted pulsed laser desorption, the matrix comprising a multihydroxylic alcohol with at least one ether bond in its carbon chain.

21. A matrix substance as in claim 20, wherein the matrix comprises at least one of diglycerol, triglycerol, and higher polyglycerols.

22. A matrix substance as in claim 20, further comprising an absorbent substance that is strongly absorbing for wavelengths output by a laser used during the matrix assisted pulsed laser desorption.

* * * * *